United States Patent
Matsuzaki et al.

(10) Patent No.: US 9,005,226 B2
(45) Date of Patent: Apr. 14, 2015

(54) FLUID EJECTION DEVICE AND METHOD TO CONTROL FLUID EJECTION DEVICE

(75) Inventors: Takahiro Matsuzaki, Shiojiri (JP); Hideki Kojima, Matsumoto (JP); Shigeo Sugimura, Okaya (JP)

(73) Assignee: Seiko Epson Corporation, Tokyo (JP)

( * ) Notice: Subject to any disclaimer, the term of this patent is extended or adjusted under 35 U.S.C. 154(b) by 609 days.

(21) Appl. No.: 12/854,698

(22) Filed: Aug. 11, 2010

(65) Prior Publication Data

US 2011/0036859 A1    Feb. 17, 2011

(30) Foreign Application Priority Data

Aug. 12, 2009   (JP) ................. 2009-187076

(51) Int. Cl.
  *A61B 17/3203*    (2006.01)
  *A61B 17/00*    (2006.01)

(52) U.S. Cl.
  CPC ... *A61B 17/3203* (2013.01); *A61B 2017/00154* (2013.01)

(58) Field of Classification Search
  CPC .................................................. A61B 17/3203
  USPC ......... 606/127, 128, 159, 161–162, 167, 170;
                                    604/30, 131, 141, 151, 246;
                                               137/565.01–565.15
  See application file for complete search history.

(56) References Cited

U.S. PATENT DOCUMENTS

| | | | |
|---|---|---|---|
| 5,643,302 A * | 7/1997 | Beiser et al. .................. | 606/167 |
| 6,820,596 B2 | 11/2004 | Namari et al. | |
| 6,860,868 B1 | 3/2005 | Sussman et al. | |
| 2002/0077585 A1 * | 6/2002 | Sussman et al. ............. | 606/166 |
| 2008/0086077 A1 | 4/2008 | Seto et al. | |
| 2008/0196762 A1 * | 8/2008 | Mallett et al. ............ | 137/565.11 |
| 2008/0289398 A1 | 11/2008 | Khashayar | |
| 2010/0069937 A1 | 3/2010 | Seto et al. | |

FOREIGN PATENT DOCUMENTS

| | | |
|---|---|---|
| EP | 2078504 A2 | 7/2009 |
| JP | 2004052596 A | 2/2004 |
| JP | 2006-118397 | 5/2006 |
| JP | 2008-082202 | 4/2008 |

* cited by examiner

*Primary Examiner* — Kathleen Holwerda
*Assistant Examiner* — Sarah W Aleman
(74) *Attorney, Agent, or Firm* — Maschoff Brennan

(57) ABSTRACT

A fluid ejection device includes a pulsating flow generation section adapted to eject a fluid in a pulsed manner; a fluid supply section adapted to supply the pulsating flow generation section with the fluid; a fluid supply tube having flexibility adapted to communicate the pulsating flow generation section and the fluid supply section with each other; and a drive control section adapted to perform drive control of the pulsating flow generation section and the fluid supply section, wherein the drive control section starts up the pulsating flow generation section, makes the fluid supply section supply the fluid at a first flow rate for a predetermined time period, and then makes the fluid supply section supply the fluid at a second flow rate lower than the first flow rate after the predetermined time period elapses.

4 Claims, 4 Drawing Sheets

FLUID EJECTION DEVICE AND METHOD TO CONTROL FLUID EJECTION DEVICE

CROSS-REFERENCE

This application claims priority to Japanese Patent Application No. 2009-187076, filed on Aug. 12, 2009, the entirety of which is hereby incorporated by reference.

BACKGROUND

1. Technical Field

The invention relates to a fluid ejection device for ejecting a fluid in a pulsed manner and a method to control the fluid ejection device.

2. Related Art

In the related art, there has been known a technology of ejecting a fluid in a pulsed manner to thereby perform ablation or excision of an object. For example, JP-A-2008-82202 discloses a fluid ejection device as a surgical instrument for incising or excising body tissue in the medical field. The fluid ejection device described in JP-A-2008-82202 includes a pulsating flow generation section having a fluid chamber with the volume changed when driving a volume changing section and converting the fluid into pulsating flow to eject it from a nozzle at high speed in a pulsed manner, a fluid supply section for supplying the pulsating flow generation section with the fluid, and a fluid supply tube for communicating the pulsating flow generation section and the fluid supply section with each other.

The pulsating flow generation section described above has the volume of the fluid chamber reduced by driving the volume changing section to thereby convert the fluid into the pulsating flow to eject it from the nozzle at high speed in a pulsed manner. Further, the pulsating flow generation section and the fluid supply section are communicated with each other via a fluid supply tube. When using the fluid ejection device as a surgical instrument, it is operated by the operator gripping the pulsating flow generation section. Therefore, the fluid supply tube having flexibility is used in order for enhancing operability.

In the case of ejecting the fluid at high speed in a pulsed manner, drive of the pulsating flow generation section causes the flow path resistance of an internal flow path of the pulsating flow generation section to increase. Since it also causes the fluid pressure inside the fluid supply tube to increase, the flexible fluid supply tube expands radially. Therefore, when starting up the pulsating flow generation section, the fluid supply rate to the pulsating flow generation section is temporarily reduced, and it takes time until a stable steady flow rate is reached. There arises a problem that a desired stable fluid ejection rate is not achievable in the period in which the fluid supply rate is reduced to be lower than the steady flow rate. The steady flow rate denotes the flow rate of the fluid supplied from the fluid supply section at a substantially constant flow rate when continuously driving the pulsating flow generation section.

SUMMARY

An advantage of some aspects of the invention is to solve at least a part of the problem described above, and the invention can be implemented as the following embodiment and aspects.

According to a first aspect of the invention, there is provided a fluid ejection device including a pulsating flow generation section adapted to eject a fluid in a pulsed manner, a fluid supply section adapted to supply the pulsating flow generation section with the fluid, a fluid supply tube having flexibility adapted to communicate the pulsating flow generation section and the fluid supply section with each other, and a drive control section adapted to perform drive control of the pulsating flow generation section and the fluid supply section, wherein the drive control section starts up the pulsating flow generation section, makes the fluid supply section supply the fluid at a first flow rate for a predetermined time period, and then makes the fluid supply section supply the fluid at a second flow rate lower than the first flow rate after the predetermined time period elapses.

According to this aspect of the invention, the fluid is supplied at the first flow rate higher than the second flow rate from the fluid supply section when the pulsating flow generation section is started up, whereby it becomes possible to prevent the temporary reduction of the rate of the fluid supplied to the pulsating flow generation section due to expansion of the fluid supply tube to thereby quickly make the rate of ejection of the fluid from the pulsating flow generation section closer to the second flow rate. Thus, it becomes possible for the pulsating flow generation section to eject the fluid at high speed in a pulsed manner at a stable fluid ejection rate immediately after the start-up of the pulsating flow generation section.

According to a second aspect of the invention, in the fluid ejection device described above, it is preferable that the drive control section determines the predetermined time period and the first flow rate taking tube information including at least one of a material, an outside diameter, a length, and a thickness of the fluid supply tube, and the second flow rate into consideration.

The first flow rate and the predetermined time period are determined taking the tube information including at least one of the material, the outside diameter, the length, the thickness (the wall thickness) as the factors for determining the expansion amount of the fluid supply tube, and the second flow rate into consideration. The expansion amount of the fluid supply tube corresponds to the reduction amount of the fluid supply to the pulsating flow generation section. By accurately increasing the rate of the fluid supplied to the pulsating flow generation section, it becomes possible to stably eject the fluid at the ejection rate immediately after the start-up of the pulsating flow generation section.

According to a third aspect of the invention, there is provided a method to control a fluid ejection device including the steps of providing a pulsating flow generation section adapted to eject a fluid in a pulsed manner, a fluid supply section adapted to supply the pulsating flow generation section with the fluid, a fluid supply tube having flexibility adapted to communicate the pulsating flow generation section and the fluid supply section with each other, and a drive control section adapted to perform drive control of the pulsating flow generation section and the fluid supply section, starting up the pulsating flow generation section, and making the fluid supply section supply the fluid at a first flow rate for a predetermined time period by the drive control section, and making the fluid supply section supply the fluid at a second flow rate lower than the first flow rate by the drive control section after the predetermined time period elapses.

According to the control method of this aspect of the invention by supplying the fluid at the first flow rate higher than the second flow rate from the fluid supply section when starting up the pulsating flow generation section, it becomes possible to prevent the reduction of the rate of the fluid supplied to the pulsating flow generation section to thereby quickly make the rate of ejection of the fluid from the pulsating flow generation section closer to the second flow rate even in the case in which the fluid supply tube expands. Thus, it becomes possible to stably eject the fluid at high speed in a pulsed manner immediately after the start-up of the pulsating flow generation section.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 2:
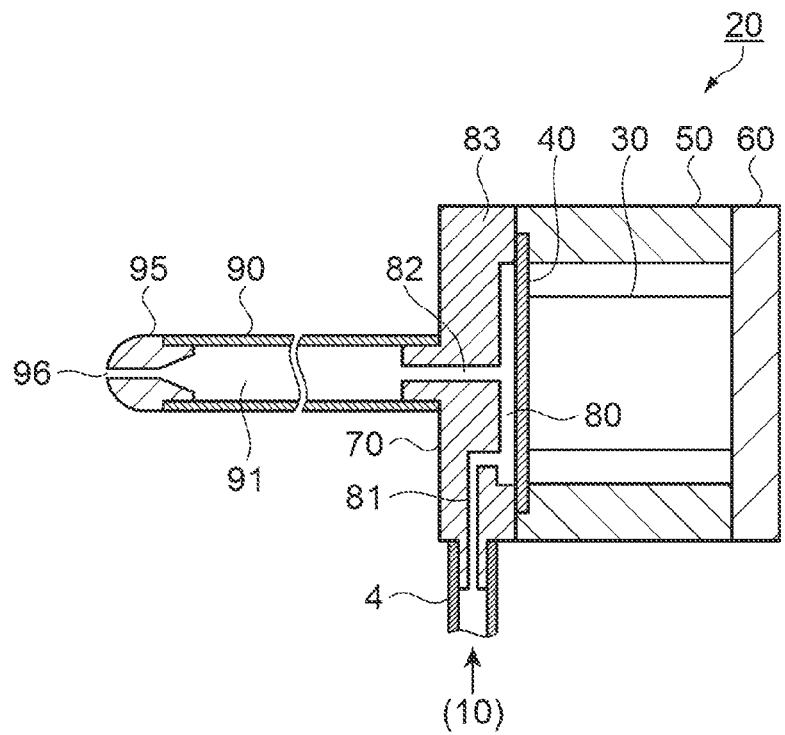
FIG. 2 is a cross-sectional diagram of a pulsating flow generation section according to the first embodiment cut along the ejection direction of a liquid.
Figure 7:
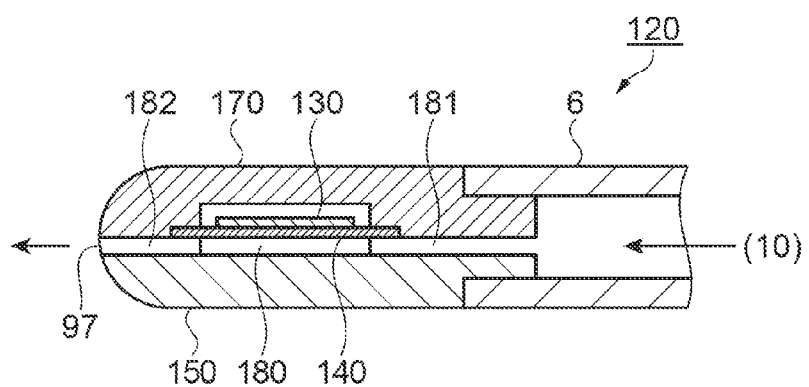
FIG. 7 is a partial side cross-sectional view showing a cut surface of the pulsating flow generation section according to a second embodiment cut in a direction perpendicular to a diaphragm.

Some embodiments of the invention will hereinafter be explained with reference to the accompanying drawings. The fluid ejection device according to the invention can be adopted as various applications such as drawing with ink or the like, cleansing of a fine matter or a fine structure, or a surgical scalpel. In the explanation of the embodiments described below, a fluid ejection device suitable for incising or excising a body tissue will be described as an example. Therefore, the fluid used in the embodiments is a liquid such as water or saline. FIGS. 2 and 7 described below are schematic diagrams having contraction scales in the vertical and horizontal directions of the members or parts different from the actual scales for the sake of convenience of illustration.

First Embodiment

Figure 1:
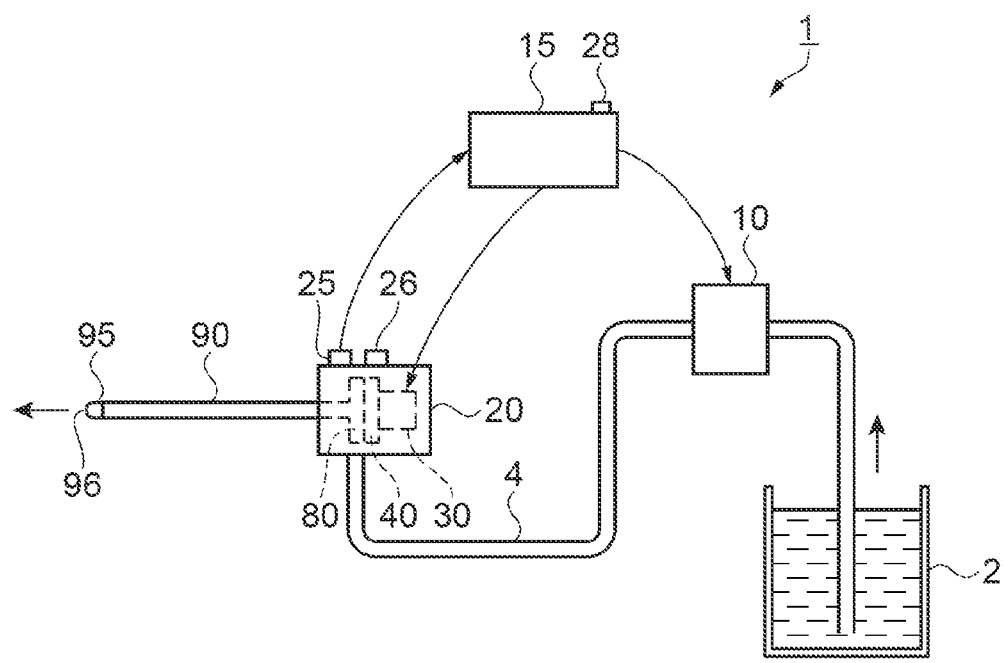
FIG. 1 is an explanatory diagram showing a configuration of a fluid ejection device according to a first embodiment.

FIG. 1 is an explanatory diagram showing a configuration of the fluid ejection device as a surgical instrument according to the first embodiment. In FIG. 1, the fluid ejection device 1 is provided with a liquid supply container 2 (hereinafter simply referred to as a container 2) for containing a liquid, a pump 10 as a fluid supply section, a pulsating flow generation section 20 for converting the liquid supplied from the pump 10 into pulsating flow to thereby eject it in a pulsed manner. The liquid supply tube 4 (hereinafter simply referred to as a tube 4) connects the pump 10 and the pulsating flow generation section 20 to each other.

A connection channel tube 90 with a thin pipy shape is connected to the pulsating flow generation section 20, and a tip portion of the connection channel tube 90 is provided with a nozzle 95 with a reduced channel diameter inserted therein.

The fluid ejection device 1 is provided with a drive control section 15, and the drive control section 15 drive-controls the pump 10 and the pulsating flow generation section 20 separately. Although the drive control section 15 is disposed at a position distant from the pump 10 and the pulsating flow generation section 20 in FIG. 1, it is also possible for the drive control section 15 to include the pump 10.

The pulsating flow generation section 20 is provided with a pulsating flow generation section start-up switch 25, and a supply flow rate switch 26 for selecting the supply flow rate from the pump 10. Since the operator operates the fluid ejection device 1 gripping the pulsating flow generation section 20 when using the fluid ejection device 1 as a surgical instrument, the pulsating flow generation section start-up switch 25 and the supply flow rate switch 26 are disposed at a position corresponding to the hand of the operator, thereby enhancing operability. It should be noted that the pulsating flow generation section start-up switch 25 controls the start-up and stop of the pulsating flow generation section 20, and the supply flow rate switch 26 controls selective switching of the steady supply rate of the pump 10.

Flowage of the liquid in the fluid ejection device 1 will briefly be explained. The liquid in the container 2 is vacuumed by the pump 10, and then supplied to the pulsating flow generation section 20 via the tube 4 at constant pressure. If the tube 4 does not expand, the liquid is supplied at a constant flow rate (referred to as a steady flow rate). The pulsating flow generation section 20 is provided with a fluid chamber 80, and a piezoelectric element 30 and a diaphragm 40 (see FIG. 2) as a volume changing section for changing the volume of the fluid chamber 80. The pulsating flow generation section 20 drives the volume changing section to change the volume of the fluid chamber 80, thereby generating the pulsating flow, and emits the liquid at high speed in a pulsed manner via the connection channel tube 90 and the nozzle 95. Here, the pulsating flow denotes the flowage of the liquid in which the liquid flows in one direction with the flow rate or the flow speed of the liquid including a periodical or irregular variation.

Although the pulsating flow includes intermittent flow of repeating flow and stop of the liquid, whether or not it is the intermittent flow does not matter providing the flow rate or the flow speed of the liquid varies periodically or irregularly. Similarly, "ejecting the liquid in a pulsed manner" denotes "ejecting the liquid having the flow rate or moving speed varying periodically or irregularly." Although the intermittent ejection in which ejection and non-ejection of the liquid are repeated can be cited as an example of the pulsed ejection, whether or not it is the intermittent ejection does not matter providing the flow rate or the moving speed of the liquid to be ejected varies periodically or irregularly. The pulsating flow generation section 20 will be described later with reference to FIG. 2.

When performing an operation using the fluid ejection device 1, the region the operator grips is the pulsating flow generation section 20. Therefore, in order for enhancing operability for the operator, it is preferable that the tube 4 is as flexible as possible. Although the rigidity of the fluid supply tube is not particularly limited, the tube having such flexibility that the fluid supply tube expands radially in accordance with the fluid pressure inside the fluid supply tube is sufficient.

A structure of the pulsating flow generation section 20 according to this embodiment will be explained.

FIG. 2 is a cross-sectional diagram of a pulsating flow generation section according to this embodiment cut along the ejection direction of the liquid. The pulsating flow generation section 20 has an entrance channel 81 for supplying the liquid to the fluid chamber 80 from the pump 10 via the tube 4, the piezoelectric element 30 and the diaphragm 40 as the volume changing section for changing the volume of the fluid chamber 80, and an exit channel 82 for delivering the liquid from the fluid chamber 80 to the fluid ejection opening section 96.

The diaphragm 40 is formed of a disk-like metal thin plate, and has a lower case 50 and an upper case 70 having peripheries adhering to each other so as to be fixed to each other. The piezoelectric element 30 in this embodiment is a stacked piezoelectric element, and has one end fixed to the diaphragm 40 and the other end fixed to a bottom plate 60.

The fluid chamber 80 is a chamber formed of a recessed section and the diaphragm 40, wherein the recessed section is provided to the surface of the upper case 70, opposed to the diaphragm 40. The exit channel 82 is opened at a substantially central part of the fluid chamber 80.

The upper case 70 and the lower case 50 are bonded integrally to each other on the respective surfaces opposed to each other. The connection channel tube 90 having a connection channel 91 communicated with the exit channel 82 is fit to the upper case 70, and the nozzle 95 is inserted into the tip portion of the connection channel tube 90. Further, the nozzle 95 is opened with a fluid ejection opening section 96 with a channel diameter reduced to be smaller than that of the exit channel 82.

The upper case 70 is provided with the entrance channel 81 communicated with the fluid chamber 80. The entrance channel 81 is attached with the tube 4.

A fluid discharge operation of the pulsating flow generation section 20 in this embodiment will be explained with reference to FIGS. 1 and 2. The fluid of the pulsating flow generation section 20 of this embodiment is discharged in accordance with the difference between the combined inertance L1 on the side of the entrance channel 81 and the combined inertance L2 on the side of the exit channel 82.

Hereinafter, the inertance will be explained.

The inertance L is expressed as $L=\rho \times h/S$ denoting the density of the fluid as $\rho$, the cross-sectional area of the channel as S, and the length of the channel as h. When denoting the pressure difference of the channel as $\Delta P$, and the flow rate of the fluid flowing through the channel as Q, the relationship of $\Delta P = L \times dQ/dt$ is derived by transforming the motion equation in the channel using the inertance L.

In other words, the inertance L represents the degree of the influence exerted to the time variation of the flow rate, and the larger the inertance L is, the smaller the time variation of the flow rate becomes, and the smaller the inertance L is, the larger the time variation of the flow rate becomes.

The combined inertance L1 on the side of the entrance channel 81 can be obtained in a range of the entrance channel 81. The combined inertance L2 on the side of the exit channel 82 can be obtained in a range of the exit channel 82.

The thickness of the tube wall of the connection channel tube 90 is arranged to provide rigidity enough for pressure propagation of the fluid.

Further, in this embodiment, the channel length and the cross-sectional area of the entrance channel 81, and the channel length and the cross-sectional area of the exit channel 82 are arranged so that the combined inertance L1 on the side of the entrance channel 81 becomes larger than the combined inertance L2 on the side of the exit channel 82.

Then, the fluid ejection operation will be explained.

The pump 10 always supplies the entrance channel 81 with the liquid at constant pressure (with a steady flow rate). As a result, when the piezoelectric element 30 does not operate, the liquid flows into the fluid chamber 80 due to the difference between the discharge force of the pump 10 and the flow path resistance of the entire channel on the entrance channel side.

When a drive signal is input to the piezoelectric element 30 and the piezoelectric element 30 rapidly expands in an normal direction of the surface of the diaphragm 40 on the side of the fluid chamber 80, the piezoelectric element 30 thus expanding presses the diaphragm 40, and the diaphragm 40 is deformed in a direction of reducing the volume of the fluid chamber 80. The pressure inside the fluid chamber 80 rises rapidly to reach several tens of atms if the combined inertances L1, L2 on the entrance channel side and the exit channel side are sufficiently large.

Since the pressure is stronger than the pressure by the pump 10 applied to the entrance channel 81, the inflow of the liquid from the entrance channel 81 into the fluid chamber 80 is reduced due to the pressure, and the outflow of the liquid from the exit channel 82 increases.

The combined inertance L1 on the entrance channel side is larger than the combined inertance L2 on the exit channel side. Therefore, an amount of increase in the liquid discharged from the exit channel 82 is larger than an amount of reduction in the liquid flowing in the fluid chamber 80 from the entrance channel 81. Thus, the pulsed liquid discharge, namely the pulsating flow, is generated in the connection channel 91. The pressure variation in the discharge operation propagates inside the connection channel tube 90 (the connection channel 91), and thus the liquid is ejected from the fluid ejection opening section 96 of the nozzle 95 at the tip thereof.

The channel diameter of the fluid ejection opening section 96 is reduced to be smaller than the channel diameter of the exit channel 82. Therefore, the liquid becomes in higher-pressure state, and is formed as pulsed droplets to be ejected at high speed.

Inside the fluid chamber 80, there is provided a vacuum state immediately after the rise in pressure due to the interaction between decrease in the amount of the liquid inflowing from the entrance channel 81 and increase in the amount of the liquid outflowing from the exit channel 82. Then, when the piezoelectric element 30 is restored to the original shape, the liquid in the entrance channel 81 flows into the fluid chamber 80 at speed equivalent to that before the operation (before the expansion) of the piezoelectric element 30 after predetermined time has elapsed due to both of the pressure of the pump 10 and the vacuum condition inside the fluid chamber 80.

After the flowage of the liquid inside the entrance channel 81 has been restored, if the expansion of the piezoelectric element 30 occurs, the pulsed droplet is continuously ejected from the fluid ejection opening section 96.

A method to control the fluid ejection device 1 according to this embodiment will be explained. Firstly, the configuration of a control system of the fluid ejection device will be explained with reference to the accompanying drawings.

Figure 3:
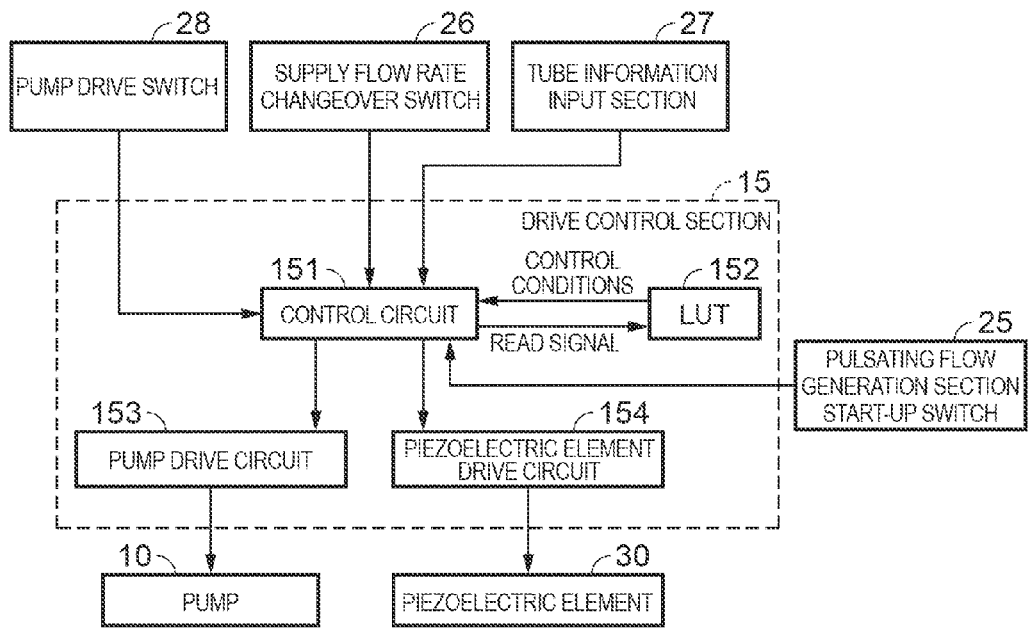
FIG. 3 is an explanatory diagram showing a schematic configuration of a control system according to the first embodiment.

FIG. 3 is an explanatory diagram showing a schematic configuration of the control system according to this embodiment. The control system includes the drive control section 15 for controlling the drive of the pump 10 and the pulsating flow generation section 20 (specifically the piezoelectric element 30), the pulsating flow generation section start-up switch 25, the supply flow rate switch 26 for the pump 10, and a pump drive switch 28.

The pulsating flow generation section start-up switch 25 and the supply flow rate switch 26 are disposed in the pulsating flow generation section 20. The pump drive switch 28 is disposed in the pump 10. The pump drive switch 28 can also be disposed to the pulsating flow generation section 20 or the drive control section 15.

The drive control section 15 has a pump drive circuit 153, a piezoelectric element drive circuit 154, and a control circuit 151 for controlling the both circuits. The drive control section 15 is further provided with a look-up table (LUT) 152. The LUT 152 includes a designated steady flow rate by the pump 10, tube information, and an incremental flow rate and incremental flow rate designation time (hereinafter also referred to simply as designation time) to be obtained afterward. Although omitted from illustration in FIG. 3, the LUT 152 is stored in a memory (storage section) such as a random access memory (RAM) or a read only memory (ROM) as the data.

The tube information is input to the control circuit 151 by a tube information input section 27. A calculation section (not shown) in the control circuit 151 obtains the incremental flow rate from the tube information and the steady flow rate to be designated, and then obtains a time period during which the incremental flow rate thus obtained is applied as the designation time, thereby forming the LUT. As the tube information input section 27, a keyboard or input switches or the like can be used. It should be noted that the LUT can also be formed previously before shipment of the fluid ejection device 1 based on the relationship between the tube information obtained by an experiment and the steady flow rate to be designated, and the incremental flow rate and the designation time during which the incremental flow rate is applied.

Then, the contents of the LUT will hereinafter be explained. Table 1 shows an example of the LUT according to this embodiment.

When operating the pulsating flow generation section start-up switch 25 to thereby start-up the pulsating flow generation section 20, the pump 10 operates in accordance with the incremental flow rate read out from the LUT 152 and the designation time thus read out therefrom during which the incremental flow rate is applied.

Control Method of Fluid Ejection Device

A method to control the fluid ejection device will be explained. Firstly, the case in which the control according to this embodiment is not performed will be explained.

Figure 4:
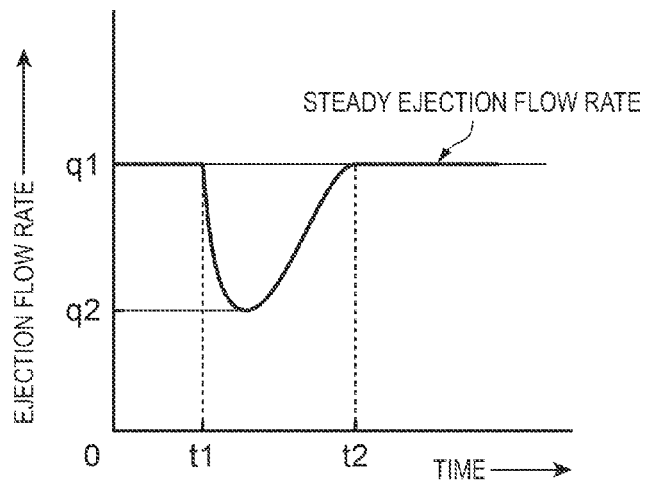
FIG. 4 is a graph schematically showing an ejection flow rate in the case in which the control according to the first embodiment is not performed.

FIG. 4 is a graph schematically showing an ejection flow rate in the case in which the control according to this embodiment is not performed. The pump 10 supplies the liquid with the steady flow rate q1 thus designated. When starting up the pulsating flow generation section 20, if the flow path resistance of the pulsating flow generation section 20 is zero or significantly small, the supply flow rate (the steady flow rate) and the ejection flow rate (the steady ejection rate) become substantially the same as each other.

When driving the piezoelectric element 30 to eject the liquid in a pulsed manner, the flow path resistance inside the pulsating flow generation section 20 increases. Since the fluid pressure in the tube 4 also increases, the tube 4 having flexibility expands radially. Thus, the rate of the fluid supplied to the pulsating flow generation section 20 is temporarily reduced to the flow rate q2, and it takes substantial time to restore the stable steady flow rate. For example, when starting up the pulsating flow generation section at the time t1, desired stable fluid ejection is not achievable in the period from the start-up to the time t2 due to decrease in the supply flow rate.

TABLE 1

| | DESIGNATED FLOW RATE (ml/h) | | | | | | | | |
|---|---|---|---|---|---|---|---|---|---|
| | 100 | | | | | | 200 | | |
| TUBE MATERIAL | A | | | B | | | A | | |
| TUBE OUTSIDE DIAMETER (mm) | 2 | 3 | 2 | 2 | 3 | 2 | 2 | 3 | 2 |
| TUBE LENGTH (mm) | 1000 | 1000 | 1500 | 1000 | 1000 | 1500 | 1000 | 1000 | 1500 |
| TUBE THICKNESS (mm) | 1 | 1 | 1 | 1 | 1 | 1 | 1 | 1 | 1 |
| CONTROL CONDITION | a1 | a2 | a3 | b4 | b5 | b6 | a4 | a5 | a6 |
| INCREMENTAL FLOW RATE (ml/h) | 30 | 35 | 40 | 40 | 45 | 45 | 40 | 45 | 50 |
| INCREMENTAL FLOW RATE DESIGNATION TIME (s) | 5 | 10 | 5 | 10 | 10 | 15 | 5 | 10 | 5 |

In this embodiment, there are obtained the designated flow rate (the steady flow rate), the tube information such as the tube material, the tube outside diameter, the tube length, and the tube thickness (the wall thickness of the tube), and control conditions, which can be obtained using the steady flow rate and the tube information, such as the incremental flow rate and the designation time during which the incremental flow rate is applied.

The steady flow rate is an element necessary for obtaining the raised pressure inside the tube. The tube material is an element for determining the physical constant (Young's modulus) of the tube.

When driving the fluid ejection device 1, the steady flow rate is designated by operating the supply flow rate switch 26, and then the pump 10 is driven by operating the pump drive switch 28. On this occasion, the tube information of the tube 4 to be used is input to the control circuit 151 using the tube information input section 27. In accordance with the read signal from the control circuit 151 based on the tube information, the control conditions of the pulsating flow generation section 20 are read out from the LUT 152.

If the flow rate of the fluid supplied to the pulsating flow generation section 20 decreases, the fluid ejection rate decreases in the period between the time t1 and the time t2. If it decreases extremely, the piezoelectric element 30 might be driven in the case in which the liquid is absent in the fluid chamber 80 in some cases.

In order for avoiding the idle driving, it is desirable to control the flow rate of the fluid supplied from the pump 10 so that the desired ejection flow rate (the steady ejection rate) is assured immediately after the start-up of the pulsating flow generation section 20.

Figure 5:
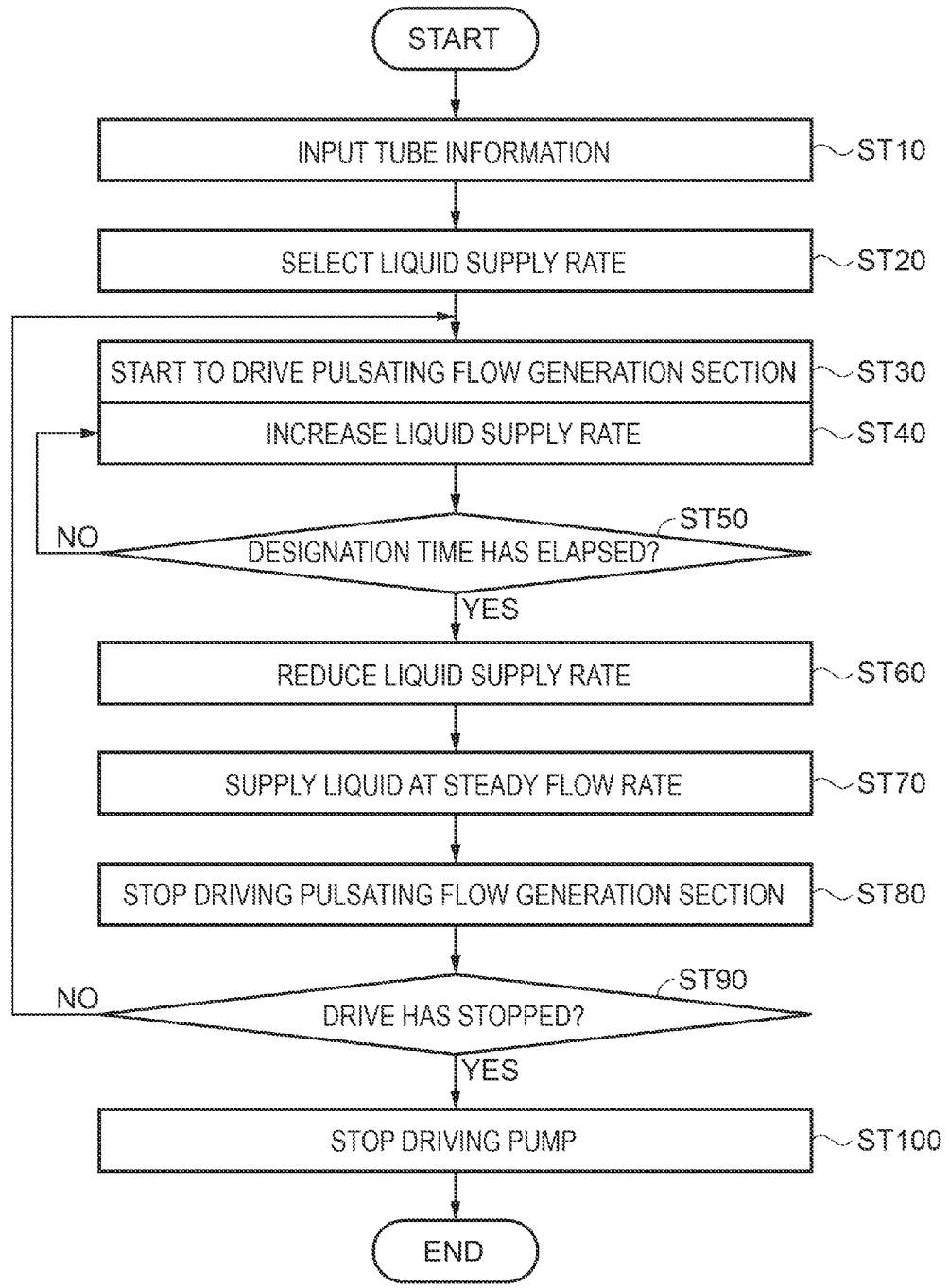
FIG. 5 is an explanatory diagram showing a flow of a method to control the fluid ejection device according to the first embodiment.

FIG. 5 is an explanatory diagram showing the flow of a method to control the fluid ejection device according to this embodiment. The explanation will be presented along the flow shown in FIG. 5. FIGS. 1, 3, and 4 are also referred to.

The control flow shown in FIG. 5 represents the flow of the control started from driving the pump 10 to start supplying the pulsating flow generation section 20 with the liquid at the steady flow rate, then starting up the pulsating flow generation section 20, continuing the steady driving (e.g., an incision of a body tissue), and then ended with stopping the pulsating flow generation section 20.

Prior to driving the pulsating flow generation section 20, the tube information input section 27 inputs the tube information to the control circuit 151 (step 10, it should be noted that "step" is hereinafter denoted as ST). It is assumed that the tube material of A, the tube outside diameter of 2 mm, the tube length of 1,000 mm, and the tube thickness of 1 mm are input as the tube information.

In the ST20, the supply flow rate switch 26 is operated to select the designated flow rate (the steady flow rate). It is assumed that 100 ml/h (ml/hour) is selected. The incremental flow rate of 30 ml/h and the designation time of 5 s (5 seconds) during which the flow rate is increased are determined based on the tube information thus input and the designated flow rate (the designated steady flow rate) (e.g., with reference to the LUT shown in Table 1).

In the ST30, the pulsating flow generation section start-up switch 25 is operated to start-up the pulsating flow generation section 20. The control circuit 151 transmits the read signal to the LUT 152 to read out the control conditions (the incremental flow rate of 30 ml/h, the designation time of 5 s).

In the ST40, the supply rate of the liquid from the pump 10 is increased based on the control conditions at substantially the same time as the start-up of the pulsating flow generation section 20. Since the incremental flow rate is 30 ml/h, the flow rate of the fluid supplied from the pump 10 becomes 130 ml/h obtained by adding the incremental flow rate of 30 ml/h to the designated steady flow rate of 100 ml/h.

In the ST50, the control circuit 151 measures the elapse of time (designation time) during which the incremental flow rate is applied to determine whether or not the designation time (5 seconds) has elapsed. In the period when the designation time of 5 seconds has not reached (NO), the supply applied with the incremental flow rate is continued. After the designation time has elapsed (YES), the state in which the supply rate of the liquid supplied from the pump 10 is reduced (ST60) to the steady flow rate is continued (ST70). The period of the ST70 corresponds to the use period of the pulsating flow generation section 20 by an operation or the like.

When halting or terminating the operation or the like, the pulsating flow generation section start-up switch 25 is operated to stop the pulsating flow generation section 20 (ST80). The pulsating flow generation section start-up switch 25 is a switch for switching between the start-up operation and the stop operation.

In the ST90, whether the fluid ejection device 1 is stopped or temporary halted is determined. If the drive thereof is to be stopped, the pump drive switch 28 is operated to stop the drive of the pump 10 (ST100).

If it is determined in the ST90 that the device is to be halted temporarily, the drive of the pump 10 is maintained without operating the pump drive switch 28. When restarting the drive of the pulsating flow generation section 20, the pulsating flow generation section start-up switch 25 is operated to start-up the pulsating flow generation section 20 (ST30). The pulsating flow generation section drive halt (ST80) period of the present case corresponds to a temporary halt period.

If the designation flow rate (the steady flow rate) is to be switched to 200 ml/h when restarting it after the temporary halt period, the supply flow rate switch 26 is operated to select 200 ml/h. It is possible to control the liquid supply rate with the increment flow rate and the designation time corresponding to the tube information thus input thereto. If the pulsating flow generation section 20 is to be driven continuously, the drive of the pump 10 and the pulsating flow generation section 20 is continued without any changes.

The fluid ejection rate according to the control method described above will be explained.

Figure 6:
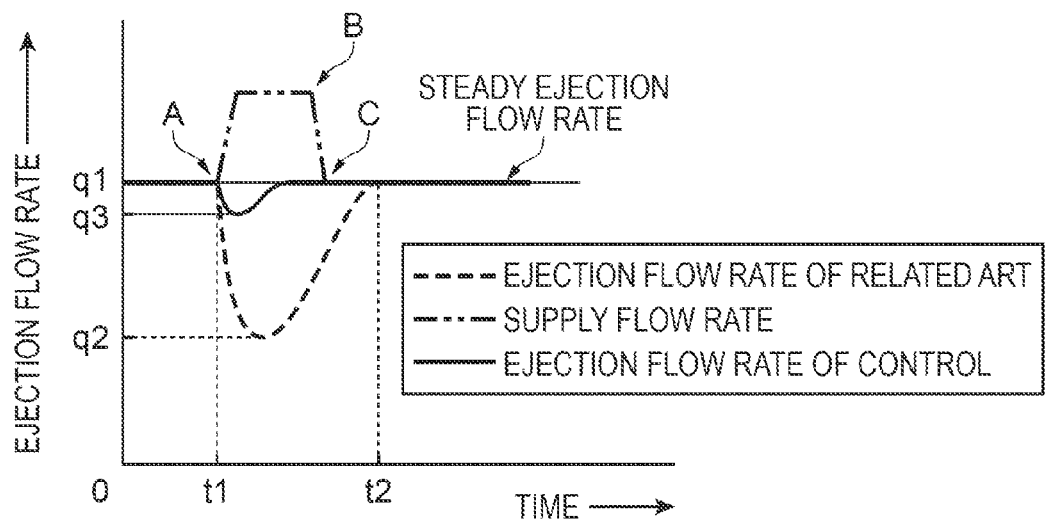
FIG. 6 is a graph schematically showing an ejection flow rate in the case in which the control according to the first embodiment is performed.

FIG. 6 is a graph schematically showing an ejection flow rate in the case in which the control according to this embodiment is performed. In this embodiment, the pump 10 increases the liquid supply rate at substantially the same time as the pulsating flow generation section is started up (indicated by A in the drawing), and then reduces the supply rate (indicated by B in the drawing) when the liquid supply rate reaches the designated incremental flow rate, and then the designated time has been reached, and restores the supply rate to the steady flow rate q1 (indicated by C in the drawing).

Therefore, the decrement q3 in the ejection rate of the liquid immediately after the start-up of the pulsating flow generation section 20 is slight compared to the decrement q2 in the ejection rate in the case in which the control according to this embodiment is not performed. Therefore, the time period from when the pulsating flow generation section 20 is started up to when the steady ejection rate is obtained can be reduced compared to the related art.

According to the fluid ejection device and the method to control the fluid ejection device described hereinabove, the pump 10 increases the fluid supply rate to be higher than the steady flow rate at substantially the same time as the pulsating flow generation section 20 is started up so as to compensate the decrement amount due to the expansion of the tube 4. By increasing the fluid supply rate, it is possible to stably eject the liquid at high speed in a pulsed manner immediately after the start-up of the pulsating flow generation section 20.

If the piezoelectric element 30 is driven in the condition in which the supply flow rate to the pulsating flow generation section 20 (specifically the fluid chamber 80) is reduced or stopped, temperature rise of the piezoelectric element 30 might be caused by the heat generation due to the insulation inside the fluid chamber 80 in addition to the heat generation due to the expansion and contraction of the piezoelectric element 30, and by the fact that the amount of liquid acting also as a cooling medium is insufficient. According to this embodiment, since the supply flow rate is assured sufficiently, the deterioration of the piezoelectric element 30 caused by the temperature rise described above can be prevented.

The pump 10 is driven based on the designation time and the incremental flow rate both obtained from the tube information and the designated steady flow rate, and is therefore able to increase the supply flow rate with accuracy, and start to eject the liquid stably immediately after the start-up of the pulsating flow generation section 20.

The designation time and the incremental flow rate are obtained using the tube information including the material, the outside diameter, the length, and the thickness of the fluid supply tube, and the steady flow rate. Since these pieces of information are input to the LUT 152, and then read out by the LUT 152 in accordance with the start-up of the pulsating flow generation section 20, the operator is not required to calculate and then input the designation time and the incremental flow rate at each operation, and therefore, the operability is improved.

Second Embodiment

The fluid ejection device according to the second embodiment will be explained with reference to the drawing. In the first embodiment described above, the configuration in the case in which the operator grips the pulsating flow generation section to operate the device is described as an example. In the second embodiment, there is a feature that the pulsating flow generation section is mounted on the tip of the tube, and is configured to be able to be inserted in a canalicular tissue such as a blood vessel. In the second embodiment, the parts common to the first embodiment are denoted with the same reference numerals, and the parts different therefrom will mainly be explained.

FIG. 7 is a partial side cross-sectional view showing a cut surface of the pulsating flow generation section according to the second embodiment cut in a direction perpendicular to a diaphragm. The pulsating flow generation section 120 is composed of an upper case 170 and a lower case 150 bonded to each other on the respective surfaces opposed to each other so as to have a tubular shape with a roughly circular cross-sectional shape. A recessed section is bored in the opposed surfaces of the lower case 150 and the upper case 170. The fluid chamber 180 is composed of the recessed section and a diaphragm 140 tightly fixed to the opposed surfaces of the upper case 170 and the lower case 150.

The lower case 150 is provided with an entrance channel 181 and an exit channel 182 formed so as to be communicated with the fluid chamber 180, and a piezoelectric element 130 is fixed on the surface of the diaphragm 140 on the side opposite to the fluid chamber 180. It should be noted that the tip portion of the exit channel 182 is opened with a fluid ejection opening section 97.

As shown in FIG. 7, in the pulsating flow generation section 120 according to the second embodiment, the entrance channel 181, the fluid chamber 180, and the exit channel 182 are arranged in a straight line. By taking the configuration described above, the wall sections, which the liquid collides with, can be reduced, and therefore, the bubbles retained in the wall sections the liquid colliding with can be reduced. As a result, it is prevented that the retained bubbles exert an influence on the pressure in the fluid chamber 180 to reduce the pressure. Thus, it is possible to stably generate the pulsating flow having sufficient excision ability.

In FIG. 7, the diaphragm 140 is disposed in parallel to the bottom surface (a surface formed of the lower case 150) of the fluid chamber 180. In other words, it can be said that the diaphragm 140 is disposed in parallel to the direction along which the liquid flows. By taking the configuration described above, it becomes possible to make the outside diameter of the pulsating flow generation section 120 substantially the same level as the outside diameter of the tube 6, and as described later, it becomes possible to insert the pulsating flow generation section 120 into a canalicular tissue such as a blood vessel.

Since the diaphragm 140 is disposed in parallel to the bottom surface of the fluid chamber 180, it becomes possible to enlarge the area of the diaphragm 140 forming the fluid chamber 180. Thus, it becomes possible to increase the amount (=displacement volume of the fluid chamber) of volume of the fluid chamber reduced due to the deformation of the diaphragm 140. For example, if the diaphragm 140 is disposed perpendicularly to the bottom surface of the fluid chamber 180, the area of the part of the fluid chamber 180, formed by the diaphragm 140, is limited to the outside diameter of the pulsating flow generation section 120. In this case, it is not achievable to increase the displacement volume of the fluid chamber due to the deformation of the diaphragm 140.

As a result, it becomes difficult to generate the pulsating flow having sufficient excision ability. In contrast, according to the configuration of the second embodiment, it becomes possible to increase the displacement volume of the fluid chamber due to the deformation of the diaphragm 140 without the limitation of the outside diameter of the pulsating flow generation section 120. Therefore, the pulsating flow having sufficient excision ability can preferably be generated.

The pulsating flow generation section 120 thus configured is connected to the tube 6. The pulsating flow generation section 120 is a device suitable for removing extraneous matter inside the canalicular tissue such as a blood vessel while being inserted in the canalicular tissue, and has an outside diameter in a range of about 2 mm through 5 mm. Therefore, the outside diameter of the tube 6 is approximately equal to the outside diameter of the pulsating flow generation section 120. Thus, it is possible to regard the tube 6 as a catheter.

Even with the pulsating flow generation section having a thin tubular shape configured as described above, advantages substantially the same as in the first embodiment described above can be obtained. A surgical instrument suitable for removing extraneous matter on the inside wall of a canalicular tissue while being inserted in the canalicular tissue can be obtained.

Further, it can also be used for cleaning the inside of the tube of a canalicular structure.

In this embodiment, the pulsating flow generation section start-up switch 25, the supply flow rate switch 26, and the pump drive switch 28 are disposed in the drive control section 15 or the pump 10.

The drive control of the fluid ejection device 1 in this embodiment can be performed by a control method the same as in the first embodiment described above.

Although in the first and second embodiments the control information is stored in the LUT 152, it is also possible to provide the tube 4 with a pressure sensor. It is also possible that the pressure sensor detects the expansion of the tube 4 based on the pressure variation, and controls the flow rate of the supply from the pump 10 based on the feedback signal.

The supply flow rate switch 26 can be a dial for directly selecting the control conditions (a1 through a6, and b4 through b6) in the LUT 152 (Table 1).

Although in the first and second embodiments the piezoelectric element presses the diaphragm to thereby generate the pulsating flow, this is not a limitation, and it is also possible to adopt any other configurations capable of generating the pulsating flow. For example, it is also possible to operate a piston (a plunger) using a piezoelectric element to reduce the volume of the fluid chamber, thereby generating the pulsating flow. It is also possible to perform a laser induction process on the liquid in the fluid chamber to make it foam (bubbles), and to generate the pulsating flow by ejecting the bubbles.

In the first embodiment described above, as an example of the LUT there is adopted the configuration of obtaining the designated flow rate (the steady flow rate), the tube information such as the tube material, the tube outside diameter, the tube length, and the tube thickness (the wall thickness of the tube), and control conditions, which can be obtained using the steady flow rate and the tube information, such as the incremental flow rate and the designation time during which the incremental flow rate is applied. However, besides the above, it is sufficient that the incremental flow rate and the designation time during which the incremental flow rate is applied can be derived from the tube to be connected thereto. For example, it is sufficient that at least either one of the tube material, the tube outside diameter, the tube length, and the tube thickness (the thickness of the wall of the tube) is included as the tube information.

In the first embodiment described above, there is adopted the configuration of referring to the LUT to determine the control conditions (the incremental flow rate and the designation time during which the incremental flow rate is applied) corresponding to the tube information input thereto. In the case in which the control conditions corresponding to the tube information input thereto do not exist in the LUT, it is also possible to obtain the control conditions regarded as the best suitable for the tube information input thereto using some interpolation calculation known to the public from a plurality of pieces of tube information and control conditions stored as the LUT. Thus, it becomes possible to derive the control conditions regarded as appropriate even in the case in which the control conditions corresponding to the tube information input to thereto do not exist in the LUT.

Although in the first embodiment described above it is configured to use the tube information input section 27 to input the tube information, this is not a limitation, but it is also possible to read an RF-ID or a barcode attached to the tube to thereby input the tube information to the control circuit 151. Thus, the trouble of the user inputting the tube information can be reduced.

What is claimed is:

1. A fluid ejection device comprising:
    a pulsating flow generation section adapted to eject a fluid in a pulsed manner from a nozzle;
    a fluid supply section adapted to supply the pulsating flow generation section with the fluid;
    a fluid supply tube having flexibility adapted to communicate the pulsating flow generation section and the fluid supply section with each other; and
    a drive control section adapted to perform drive control of the pulsating flow generation section and the fluid supply section,
    wherein the pulsating flow generation section has an entrance channel which communicates with the fluid supply tube and an exit channel which communicates with the nozzle,
    wherein an inertance of the entrance channel is larger than an inertance of the exit channel,
    wherein the drive control section starts up the pulsating flow generation section, makes the fluid supply section supply the fluid to the pulsating flow generation section at a steady first flow rate for a predetermined time period, and then makes the fluid supply section supply the fluid to the pulsating flow generation section at a steady second flow rate lower than the first flow rate after the predetermined time period elapses, wherein both the steady first flow rate and the steady second flow rate are positive flow rates.

2. The fluid ejection device according to claim 1, wherein the drive control section determines the predetermined time period and the first flow rate using tube information including at least one of a material, an outside diameter, a length, and a thickness of the fluid supply tube, and the second flow rate.

3. A surgical instrument, comprising the fluid ejection device according to claim 1.

4. A method to control a fluid ejection device comprising:
    providing a pulsating flow generation section adapted to eject a fluid in a pulsed manner from a nozzle, a fluid supply section adapted to supply the pulsating flow generation section with the fluid, a fluid supply tube having flexibility adapted to communicate the pulsating flow generation section and the fluid supply section with each other, and a drive control section adapted to perform drive control of the pulsating flow generation section and the fluid supply section;
    starting up the pulsating flow generation section, and making the fluid supply section supply the fluid to the pulsating flow generation section at a steady first flow rate for a predetermined time period by the drive control section; and
    making the fluid supply section supply the fluid to the pulsating flow generation section at a steady second flow rate which is lower than the first flow rate after the predetermined time period elapses by the drive control section driving the fluid supply section,
    wherein the pulsating flow generation section has an entrance channel which communicates with the fluid supply tube and an exit channel which communicates with the nozzle,
    wherein an inertance of the entrance channel is larger than an inertance of the exit channel,
    wherein both the steady first flow rate and the steady second flow rate are positive flow rates.

* * * * *